United States Patent
Green et al.

(10) Patent No.: US 9,658,202 B2
(45) Date of Patent: May 23, 2017

(54) TAGGING METHOD

(75) Inventors: Darrell Green, Yarm (GB); Duncan William John McCallien, Darlington (GB); Christopher Thomas Llewellyn, Darlington (GB)

(73) Assignee: JOHNSON MATTHEY PLC, London (GB)

( * ) Notice: Subject to any disclaimer, the term of this patent is extended or adjusted under 35 U.S.C. 154(b) by 404 days.

(21) Appl. No.: 12/680,317

(22) PCT Filed: Aug. 4, 2008

(86) PCT No.: PCT/GB2008/050656
§ 371 (c)(1),
(2), (4) Date: Jun. 4, 2010

(87) PCT Pub. No.: WO2009/040563
PCT Pub. Date: Apr. 2, 2009

(65) Prior Publication Data
US 2010/0297774 A1 Nov. 25, 2010

(30) Foreign Application Priority Data
Sep. 28, 2007 (GB) .................................. 0718934.3

(51) Int. Cl.
*G01N 37/00* (2006.01)
*G01N 33/03* (2006.01)
(Continued)

(52) U.S. Cl.
CPC ............. *G01N 33/03* (2013.01); *G01N 30/02* (2013.01); *G01N 30/72* (2013.01); *Y10T 436/13* (2015.01)

(58) Field of Classification Search
None
See application file for complete search history.

(56) References Cited

U.S. PATENT DOCUMENTS 4,764,290 A   8/1988 Currey
5,984,983 A * 11/1999 Asgaonkar et al. ............ 44/385
(Continued)

FOREIGN PATENT DOCUMENTS

DE  10 2004 031 486 A1  1/2006
JP     2002-513155 A    5/2002
(Continued)

OTHER PUBLICATIONS

Enoiu et al., "Gas and liquid chromatography-mass spectrometry of aldehydic products from lipid peroxidation," *Analusis*, 2000, 28 (4), pp. 285-290.
(Continued)

*Primary Examiner* — Robert Xu
(74) *Attorney, Agent, or Firm* — RatnerPrestia

(57) ABSTRACT

A method of identifying a product comprises forming a tagged product by adding to said product a tracer material comprising at least one tracer compound which is acceptable for use as an additive in food and subsequently analyzing a sample of said product to determine the presence of said tracer compound thereby to determine whether said sample is a sample of the tagged product. The method is especially useful for the identification of vegetable oil products from sustainably managed sources. The use of permitted food additives as tracers enables the product to be identified in the supply chain while also allowing it to be used safely in foodstuffs if required.

15 Claims, 2 Drawing Sheets

(51) Int. Cl.
    *G01N 30/02*     (2006.01)
    *G01N 30/72*     (2006.01)

(56) References Cited

U.S. PATENT DOCUMENTS

| | | |
|---|---|---|
| 6,312,958 B1 | 11/2001 | Meyer et al. |
| 2004/0029295 A1 | 2/2004 | Brogger et al. |
| 2004/0081587 A1 | 4/2004 | Melker et al. |

FOREIGN PATENT DOCUMENTS

| | | |
|---|---|---|
| RU | 2 040 791 C1 | 7/1995 |
| WO | WO-95/06249 A1 | 3/1995 |
| WO | WO-96/17954 A1 | 6/1996 |
| WO | WO-2006/075953 A1 | 7/2006 |

OTHER PUBLICATIONS

Title 21: Food and Drugs, Part 172—Food Additives Permitted for Direct Addition to Food for Human Consumption, searched on Feb. 22, 2013, URL:http://www.ecfr.gov/cgi-bin/text-idx?c=ecfr&sid=2cc4ded2a884fffdd7a330def450058f&rgn=div5&view=text&node=21:3.0.1. 1.3&idno=21#21:3.0.1.1.3.1.1.1.

\* cited by examiner

TAGGING METHOD

CROSS-REFERENCE TO RELATED APPLICATIONS

This application is the U.S. National Phase application of PCT International Application No. PCT/GB2008/050656, filed Aug. 4, 2008, and claims priority of British Patent Application No. 0718934.3, filed Sep. 28, 2007, the disclosures of both of which are incorporated herein by reference in their entirety.

FIELD OF THE INVENTION

The present invention relates to a method of tagging a natural product and methods of identifying such a product using the tagging method. The invention is particularly concerned with a method of tagging a natural product which has been produced in a particular way or at a particular location.

BACKGROUND OF THE INVENTION

The introduction and availability of products which are produced in an economically and environmentally sustainable manner are currently of great interest commercially. The growing political pressure to reduce the consumption of fossil fuels has increased the production and consumption of alternative fuels such as those manufactured from renewable resources, in particular biodiesel. Biodiesel comprises methyl esters of long-chain fatty acids and is produced from vegetable oils (triglycerides) by a trans-esterification reaction with methanol. A problem with the increased consumption of biodiesel is that large amounts of land are required to grow the oil-bearing crops from which the vegetable oil is produced. When the biodiesel crops are grown on land which has been illegally cleared or diverted from food production then its production may have undesirable consequences for the environment and biodiversity. There is therefore a need to provide a method of identifying vegetable oils which have been produced in a sustainable manner. It is an object of the invention to provide such a method.

SUMMARY OF THE INVENTION

According to the invention, a method of identifying a product comprises forming a tagged product by adding to said product a tracer material comprising at least one tracer compound which is acceptable for use as an additive in food and subsequently analysing a sample of said product to determine the presence of said tracer compound thereby to determine whether said sample is a sample of the tagged product. The concept of tagging edible products such as foodstuffs is discussed in US 2004/0029295 where planar microparticles embossed with optically recognizable indicia are used as the taggants. The microparticles consist of polymeric material generally regarded as safe (GRAS) by the US Food and Drug Administration: detection is by visual techniques such as microscopy or fluorescence. Similarly, US 2004/081587 discusses a solution for identifying whether medication has been taken by a patient by using flavourings permitted for use in foods. The flavourings are selected for their low solubility in aqueous media, such as those found in the body, and also for their relatively high volatility. This means that trace amounts of the flavourings can be detected in the breath exhaled by the patient.

A preferred application of the method is for the identification of a bio-derived natural product, i.e. a composition which is or is derived from a vegetable or animal source. Such products include vegetable oils and animal fats, in particular those suitable for use as fuel or as a feedstock for the manufacture of fuel such as biodiesel. Alternative applications include the tagging and identification of alcohols, particularly ethanol and methanol which are used as fuels, for example as "gasohol", a mixture of gasoline and ethanol. Other liquid products may also be tagged and identified by the method of the invention. By "tagging" we mean the adding of an identifiable tracer or tag to the product to form a tagged product, the tracer being capable of being subsequently identified in a sample of the product, by chemical analysis or otherwise, in order to confirm the identity of the sample as a sample of the tagged product.

BRIEF DESCRIPTION OF THE DRAWINGS

The invention will be further described by reference to the figures in which.

DETAILED DESCRIPTION OF THE INVENTION

Figure 1:
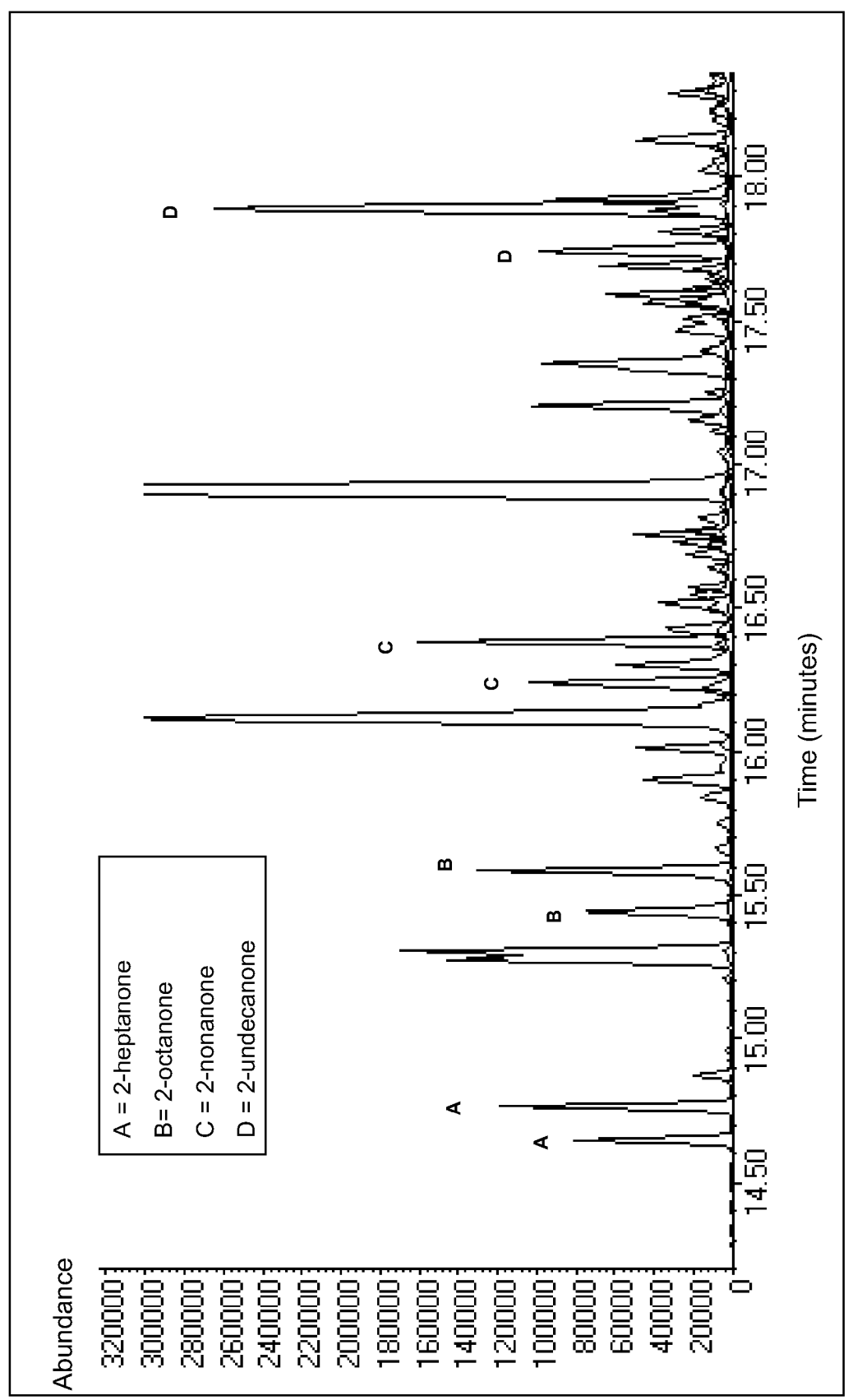
FIG. 1 shows an overlay of each extracted ion chromatogram for Example 1.

Whilst the tracer material may be incorporated in or coated on a solid product, the method is particularly suitable for tagging liquid products, or solid products in which a tracer material can be dispersed whilst in a softened or molten state. It is preferred that the resulting tagged product comprises a homogeneous or near-homogeneous mixture of the tracer material and the product. In a particular embodiment, the invention is suitable for tagging and identifying oils derived from animal or vegetable sources, including as examples, palm oil and oils derived from soybeans and corn The tracer is preferably added to the oil when the fruit is crushed or shortly afterwards. Alternatively the tracer may be added to the oil after initial processing in order to avoid degrading the tracer compound or compounds in a processing step. The tracer is preferably added to the crude oil before it is removed from its source in order that the tracer may be reliably associated with the source. To this effect, each source of origin, whether a region or an individual producer may have its own unique tracer material. In this way the identity and source of a batch of oil may be determined by analysis of the tracer at any subsequent stage of processing, whether the oil is used for the manufacture of a fuel or for any other purpose.

The tracer material comprises at least one tracer compound which is acceptable for use as an additive in food, as a preservative, anti-caking agent, coating, nutritional additive, gum, or preferably as a flavouring. Preferably the tracer comprises a compound which is listed as a permissible food additive by the US Food and Drug Administration (FDA) and/or the relevant organisation appointed by the European Commission and/or other organisation charged with regulating the use of additives in foods in any region or any organisation replacing the above-named organisations to fulfil their function. In particular suitable compounds comprise those compounds listed in:

(i) 1999/217/EC: "Commission Decision of 23 Feb. 1999 adopting a register of flavouring substances used in or on foodstuffs drawn up in application of Regulation (EC) No 2232/96 of the European Parliament and of the Council of 28 Oct. 1996", and/or (ii) US Code Title 21—Food and Drugs, Chapter 1 Subchapter B Part 172—"Food Additives Permitted for Direct Addition to Food for Human Consumption Subpart F—Flavoring Agents and Related Substances Sec. 172.515 Synthetic Flavoring Substances and Adjuvants".

The reference to the relevant lists includes reference to updates and amendments to the lists which may appear from time-to-time. Preferably the tracer compound has achieved GRAS ("generally regarded as safe") status on review by an organisation such as the Flavor and Extract Manufacturers Association (FEMA). By selecting as tracer compounds those materials which are known to be safe for addition to food products, it is possible to tag the product with an identifiable tracer whilst allowing the tagged product to be used in foods if required.

The tracer compound may comprise nitrogen- and/or sulphur-containing heterocycles. Suitable tracer compounds from this class include: —pyrazinyl methyl sulfide, 2,3-dimethylpyrazine, 2,3-diethyl-5-methylpyrazine, 5-acetyl-2,4-dimethylthiazole. The preferred tracer compounds comprise carbonyl compounds. Ketones are especially preferred because they are less susceptible to oxidation and other forms of degradation over time than aldehydes. Furthermore, it is known that naturally occurring fats and oils may oxidise in air, resulting in an increase in the level of certain aldehydic species over time, making the use of aldehydes as tracers less preferred. Esters and lactones occur naturally in oils and fats and so they are not preferred tracer compounds for use in vegetable oils. The most preferred tracer compounds comprise aromatic or aliphatic ketones which are saturated or which contain $\alpha,\beta$-unsaturation. Dicarbonyl compounds are less preferred. Suitable tracer compounds include: —pentan-2-one, 4-methylpentan-2-one, 4-hexen-3-one, heptan-2-one, heptan-3-one, heptan-4-one, 6-methyl-heptan-3-one, 2,6-dimethylheptan-4-one, octan-2-one, octan-3-one, nonan-2-one, nonan-3-one, decan-2-one, undecan-2-one, undecan-6-one, pent-3-en-2-one, hex-4-en-3-one, 2-methyl-3-heptanone, 5-methyl-2-hepten-4-one, 2,6-dimethyl-4-heptanone, 6-methylhept-5-en-2-one, oct-1-en-3-one, oct-2-en-4-one, oct-3-en-2-one, dec-3-en-2-one, 4-phenyl-3-buten-2-one, ethyl vinyl ketone, cyclohexanone, cyclohex-2-en-one, acetophenone, alpha-ionone, camphor, carvone, damascenone, beta-damascone, fenchone, geranylacetone, iso-menthone, nootkatone, zingerone.

The tracer compound may comprise a natural product or a synthetic product, including a synthetic version of a naturally occurring compound. The tracer compound may be selected to be a compound which is absent from the product to be tagged in its un-tagged form. Alternatively, the tracer compound may comprise a compound which is naturally occurring in the untagged product at a lower level than the concentration of the tracer compound. The tracer compound is preferably selected to be of low volatility such that no loss of tracer may occur through evaporation under the conditions of storage and transport of the product, to an extent which would significantly affect the concentration of tracer in the product. The tracer material may contain more than one tracer compound but preferably contains less than twenty tracer compounds. It is preferred to use at least two tracers, preferably between two and twelve tracers in the tracer material. When the tracer material contains more than one tracer compound, the number of different tracer materials available is increased because each tracer material may be identified not only from the presence of each tracer compound but also from the relative amount of each tracer compound present. Therefore it is possible to formulate a very large number of tracer materials from a relatively limited number of suitable tracer compounds. This opens the possibility that each producer may be associated with a unique tracer material to identify their product through the supply chain.

The tracer material may optionally contain additional ingredients such as other tracers, dyes, compatibilisers, solvents, diluents etc. A suitable diluent may comprise a material of a similar nature to the product to be tagged, e.g. the tracer compound may be dispersed in a sample of a suitable vegetable oil when the tracer material is intended for tagging vegetable oil products. Pre-dispersal of the tracer compound in such a composition may make thorough dispersal of the tracer in the product easier. Metering pumps usually only operate in the parts per million range, hence dilution of a tracer that will be present at parts per billion is essential. Furthermore, blending of the proposed tracers in a sample of the oil to be tagged will make them more convenient to handle, as some of the tracers are flammable liquids when neat. The tracer material is preferably a liquid and is preferably added to the product by a reliable method suitable for dispensing a predetermined, relatively small amount of the tracer material into the product. A metering pump is suitable for use in adding the tracer material to the product. As an alternative, the tracer material may be provided in predetermined quantities or aliquots packaged in individual containers or in a dispersible capsule or pellet. When a dispersible capsule, pellet or tablet is used, the dispersant or capsule material is preferably formed from a material which may remain in the product without rendering it unsuitable for further processing or for food use, if required. Such a material may be a waxy solid formed from a high molecular weight or saturated/hardened oil or fat. Some crude natural oils may be almost solid at 20-25° C. or even up to 50-60° C., so it may be necessary to warm them to their liquid state before adding the tracer material to ensure that thorough blending and dispersion can occur.

The tracer compound or compounds selected must be detectable in the product material at a low level of concentration by an available method of analysis. Therefore the concentration of each tracer compound in the product must be greater than the limit of detection for that compound of the selected analytical method. The concentration of each tracer must also be significantly higher than any amount that might occur naturally. The concentration of the tracer compound in the product is not more than the concentration at which the use of the compound as an additive for food has been approved and is usually less than the approved concentration. Usually the tracer material is added to the product at a level at which the or each tracer compound is present in the product at a concentration 5 ppb-5 ppm, preferably in the range from about 10-1000 ppb, more preferably 50-500 ppb. The amount of tracer material added to the product is preferably calculated to provide a predetermined concentration of the or each tracer compound in the product, the concentration or relative concentration of each tracer compound being selected to provide an identifiable characteristic to the tagged product.

Each tracer compound is detectable, preferably quantitatively, in a sample of the product by a suitable method of analysis. Preferred analytical methods include chromatography, in particular liquid chromatography, HPLC, and gas chromatography GC, coupled with a suitable detector. A particularly preferred analytical method for use in the invention is gas chromatography coupled with a suitable detector.

A preferred detector for nitrogen and sulphur heterocycles coupled to a GC is a pulsed flame photometric detector, thus making the technique GC-PFPD. A preferred detector for carbonyl containing compounds is a mass spectrometer, thus making the technique GC-MS. The tagged product sample may be subjected to one or more preparative steps such as separation, derivatisation, concentration etc, before analysis depending on the nature of the tracer compound(s), the product and the analytical method selected. Optionally, an internal reference material can also be included in the sample prior to its analysis. The tracer compounds may be separated from the product sample prior to analysis and in a preferred embodiment of the method, extraction into a suitable solvent is carried out. The solvent is selected to be immiscible with the product sample and to provide a suitable matrix for the subsequent step(s) in the analysis. As an alternative, the tagged product sample may be heated in a container and a sample of the headspace taken for analysis, e.g. by injection into a chromatography column. The tracer compounds may optionally be derivatised from the product sample or from an extracted portion of the product sample prior to analysis. When the product is an oil or fat then the tracer compounds are normally first extracted into a more mobile liquid which is miscible with the derivatisation reagent. Derivatisation, when used, is selected to enhance the ability of the analytical method to separate and/or identify the tracer compounds present compared with other compounds present in the sample. A skilled analyst is capable of selecting the sample treatment steps and particular derivatisation reagents appropriate to the method used.

As an example, a suitable analytical method will be described applied to one preferred embodiment of the method of the invention which is for use in the detection of at least one tracer compound comprising a ketone dispersed in palm oil. In a first step, all tracer compounds present are extracted from the oil by extraction into methanol. Methanol is selected to be immiscible with the palm oil but miscible with the aqueous derivatisation reagent and provides a good solvent for the tracer compounds. An alternative suitable solvent may be selected. The methanol layer containing the tracer compounds is collected. Then the tracer compounds are derivatised by reacting the extracted methanolic solution with an aqueous solution of O-(2,3,4,5,6-pentafluorobenzyl) hydroxylamine hydrochloride (PFBHA) to produce the corresponding pentafluorobenzyl oxime derivatives. Finally, the derivative is extracted into an organic phase, such as chloroform, for analysis and concentration. The organic layer containing the derivative is removed, usually dried, and then analysed by GC/MS. The derivatives are easier to detect with typical detectors that may be attached to a GC than the original ketones because, being fluorine-containing, they are more massive and also quite different chemically from any background matrix that may also have been co-extracted. Typical detectors that may be attached to a GC apparatus to analyse for the pentafluorobenzyl oxime derivatives include electron capture detectors, halogen specific detectors and mass spectrometers, operating in a negative ion mode. Although the pentafluorobenzyl oxime derivatives can have significantly longer elution times than the underivatised tracers, the elution times should not be so extended for the major components of the palm oil to swamp the tracer derivative signals. Further, the oxime derivatives of the tracers have a characteristic spectrum which is more easily recognised and quantified than that of the underivatised tracers. Alternatively, other suitable derivatising reagents for carbonyl compounds may be selected by the skilled person, possibly after some routine experimentation. 2,4-dinitrophenylhydrazine may be used as an alternative derivatising agent but it is less preferred because, in trials, the tracer derivatives were less readily distinguishable from the background matrix, particularly when the detector was a mass spectrometer running in electron impact mode. The skilled person may select an alternative method of treatment and analysis which is calculated to provide a qualitative, or preferably at least semi-quantitative, determination of the tracer compounds in the sample. It is also possible to analyse the tracer compounds in the product directly. Where the product is an oil or fat, it is greatly preferred to extract the tracer compound to avoid the build-up of deposits of fatty residues on the analytical apparatus, particularly the chromatography column.

EXAMPLES

The invention will be further described in the following examples.

Example 1

2-Heptanone, 2-octanone, 2-nonanone and 2-undecanone were each dissolved in crude palm oil at a concentration of 500 ppb. 10 mL of the tagged oil was then extracted with 5 mL of methanol whilst stirring for 1 hour at 60° C. The extract containing the tags was removed. 5 mL of 1 mg/mL aqueous O-(2,3,4,5,6-pentafluorobenzyl)hydroxylamine hydrochloride (PFBHA) was added to the extract and incubated for 2 hours at 60° C. with vigorous stirring. The reaction mixture was then extracted with 2.5 mL chloroform whilst stirring for 20 minutes at 60° C. The chloroform layer containing the derivatives was removed and dried through a cotton wool plug prior to analysis by GC/MS in negative chemical ionisation (NCI) mode. The GC/MS instrumentation used was an Agilent® 6890 GC with Agilent 5973 Mass Selective Detector equipped with J&W Scientific™ HP-5 capillary column (30 m length, 0.32 mm i.d., 0.25 mm stationary phase thickness). The initial oven temperature was 50° C. which was held for 5 minutes, then ramped at 16.67° C./min to 300° C. and held for 20 minutes. Using these conditions analysis is carried out in NCI mode with methane as the reagent gas. The ion source and quadrupole temperatures were set to 154° C. and 150° C. respectively. Ion masses corresponding to [M-20] are monitored in selected ion monitoring (SIM) mode to identify individual tags. For each ion of interest an extracted ion chromatogram was used to measure the peak areas. For the derivatives of the 2-heptanone, 2-octanone, 2-nonanone and 2-undecanone tracers, signals of m/e 289, 303, 317 and 345 respectively were monitored. FIG. 1 shows an overlay of each extracted ion chromatogram.

Example 2

Figure 2A:
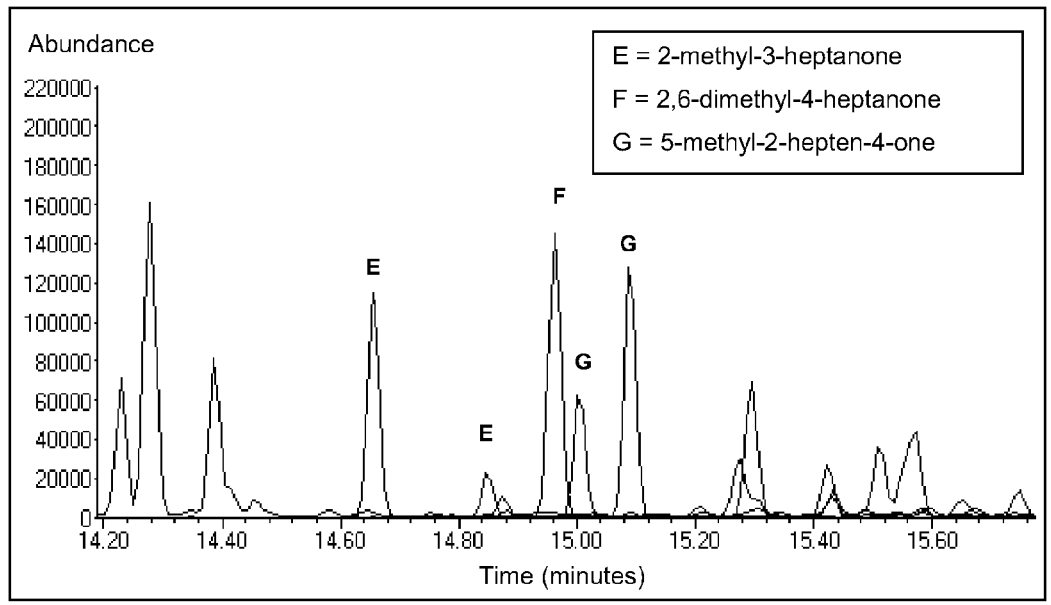
FIGS. 2a and 2b show overlays of each extracted chromatogram for Example 2.
Figure 2B:
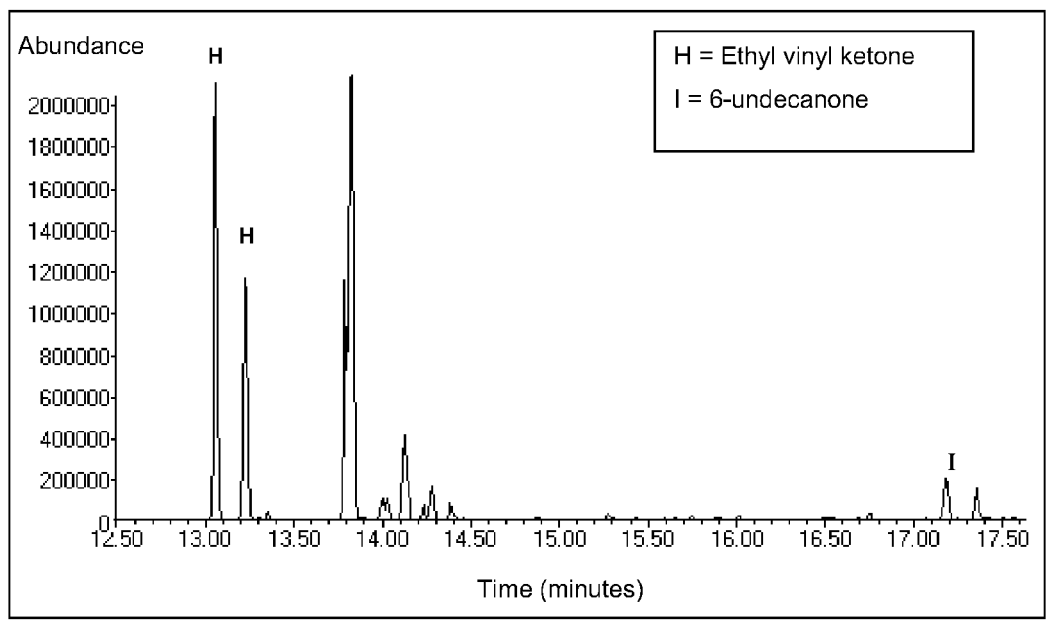

2-Methyl-3-heptanone, 6-undecanone, ethyl vinyl ketone, 5-methyl-2-hepten-4-one and 2,6-dimethyl-4-heptanone were each dissolved in crude palm oil at a concentration of 500 ppb. 10 mL of the tagged oil was then extracted with 5 mL of methanol whilst stirring for 1 hour at 60° C. The extract containing the tags was removed. 5 mL of 1 mg/mL aqueous O-(2,3,4,5,6-pentafluorobenzyl)hydroxylamine hydrochloride (PFBHA) was added to the extract and incubated for 2 hours at 60° C. The reaction mixture was then extracted with 2.5 mL chloroform whilst stirring for 20 minutes at 60° C. The chloroform layer containing the derivatives was removed and dried through a cotton wool plug prior to analysis by GC/MS using the same apparatus and method as described in Example 1. For the derivatives of 2-methyl-3-heptanone, 6-undecanone, ethyl vinyl ketone, 5-methyl-2-hepten-4-one and 2,6-dimethyl-4-heptanone signals of m/e 303, 345, 259, 301 and 317 respectively were monitored. FIGS. 2a and 2b show overlays of each extracted ion chromatogram.

Although the procedures described in the examples involve repeated manipulations, quantification of the tracer compounds is still possible. The relative standard deviation (RSD) of the response for the compounds mentioned in examples 1) and 2) was found to be on average 5-6%. This RSD was obtained by applying the analysis procedure described to each of the tracer compounds cited in the examples, either in combination or singly, in five separate samples. Furthermore, knowing the uncertainty associated with the methodology quoted in the examples allows the tracer compounds to be monitored over an extended period and a conclusion drawn as to their stability or otherwise. No noticeable degradation was observed when the tracer compounds are present in an oil even on storage at 40° C. over six weeks. Furthermore, no separation of the tracer compounds occurred from the oil when stored below ambient temperature.

The invention claimed is:

1. A method of identifying a product comprises forming a tagged product by adding to said product a tracer material comprising at least one tracer compound comprising a carbonyl compound which is acceptable for use as an additive in food and subsequently analysing a sample of said product to determine the presence of said tracer compound thereby to determine whether said sample is a sample of the tagged product, wherein the product comprises a bio-derived natural product selected from the group consisting of an oil or fat derived from a vegetable or animal source,
    wherein said analysis is performed by chromatography, and
    wherein the at least one tracer compound present in the sample is separated from the product or derivatised prior to analysis.

2. A method according to claim 1, wherein the at least one tracer compound comprises a ketone.

3. A method according to claim 2, wherein said ketone is selected from the group consisting of pentan-2-one, 4-methylpentan-2-one, 4-hexen-3-one, heptan-2-one, heptan-3-one, heptan-4-one, 6-methylheptan-3-one, 2,6-dimethylheptan-4-one, octan-2-one, octan-3-one, nonan-2-one, nonan-3-one, decan-2-one, undecan-2-one, undecan-6-one, pent-3-en-2-one, hex-4-en-3-one, 2-methyl-3-heptanone, 5-methyl-2-hepten-4-one, 2,6-dimethyl-4-heptanone, 6-methylhept-5-en-2-one, oct-1-en-3-one, oct-2-en-4-one, oct-3-en-2-one, dec-3-en-2-one, 4-phenyl-3-buten-2-one, ethyl vinyl ketone, cyclohexanone, cyclohex-2-en-one, acetophenone, alpha-ionone, camphor, carvone, damascenone, beta-damascone, fenchone, geranylacetone, iso-menthone, nootkatone and zingerone.

4. A method according to claim 1 wherein said tracer compound comprises a nitrogen- and/or sulphur-containing heterocycle.

5. A method according to claim 4, wherein said tracer compound is selected from the group consisting of pyrazinyl methyl sulfide, 2,3-dimethylpyrazine, 2,3-diethyl-5-methylpyrazine and 5-acetyl-2,4-dimethylthiazole.

6. A method according to claim 1, wherein the tracer material is added to the product in an amount calculated to provide a predetermined concentration of the or each tracer compound in the product.

7. A method according to claim 6, wherein the tracer material is added to the product in an amount calculated to provide a concentration of the or each tracer compound in the product at a concentration in the range from 5 ppb-5 ppm.

8. A method according to claim 1, wherein the tracer material comprises more than one tracer compound, the relative amounts of the tracer compounds being selected to provide an identifiable characteristic to the tagged product, and the analysis of the sample is performed in order to identify the presence of the tracer material through the identification of the characteristic relative amounts of the tracer compounds.

9. A method according to claim 8, wherein the tracer material contains from two to twelve tracer compounds.

10. A method according claim 1, wherein said analysis is performed by a method selected from liquid chromatography, gas chromatography, a combination of gas chromatography coupled with a pulsed flame photometric detector, and a combination of gas chromatography coupled with a mass spectrometer.

11. A method according to claim 7, wherein the tracer material is added to the product in an amount calculated to provides a concentration of the or each tracer compound in the product at a concentration in the range from 10-1000 ppb.

12. A method according to claim 11, wherein the tracer material is added to the product in an amount calculated to provides a concentration of the or each tracer compound in the product at a concentration in the range from 50-500 ppb.

13. A method according to claim 1, wherein the at least one tracer compound is selected from a compound which is listed as a permissible food additive by the US Food and Drug Administration (FDA).

14. A method of identifying a product comprises forming a tagged product by adding to said product a tracer material comprising at least one tracer compound comprising a carbonyl compound which is acceptable for use as an additive in food and subsequently analysing a sample of said product to determine the presence of said tracer compound thereby to determine whether said sample is a sample of the tagged product,
    wherein the product comprises a bio-derived natural product selected from the group consisting of an oil or fat derived from a vegetable or animal source, and
    wherein the at least one tracer compound is selected from the group consisting of pentan-2-one, 4-methylpentan-2-one, 4-hexen-3-one, heptan-2-one, heptan-3-one, heptan-4-one, 6-methylheptan-3-one, 2,6-dimethylheptan-4-one, octan-2-one, octan-3-one, nonan-2-one, nonan-3-one, decan-2-one, undecan-2-one, undecan-6-one, pent-3-en-2-one, hex-4-en-3-one, 2-methyl-3-heptanone, 5-methyl-2-hepten-4-one, 2,6-dimethyl-4-heptanone, 6-methylhept-5-en-2-one, oct-1-en-3-one, oct-2-en-4-one, oct-3-en-2-one, dec-3-en-2-one, 4-phenyl-3-buten-2-one, ethyl vinyl ketone, cyclohexanone, cyclohex-2-en-one, acetophenone, alpha-ionone, camphor, carvone, damascenone, beta-damascone, fenchone, geranylacetone, iso-menthone, nootkatone and zingerone.

15. A method of identifying a product comprises forming a tagged product by adding to said product a tracer material comprising at least one tracer compound comprising a carbonyl compound which is acceptable for use as an additive in food and subsequently analysing a sample of said product to determine the presence of said tracer compound thereby to determine whether said sample is a sample of the tagged product, wherein the product comprises a bio-derived natural product selected from the group consisting of an oil or fat derived from a vegetable or animal source, and wherein the at least one tracer compound is selected from the group consisting of pentan-2-one, 4-methylpentan-2-one, 4-hexen-3-one, heptan-2-one, heptan-3-one, heptan-4-one, 6-methylheptan-3-one, 2,6-dimethylheptan-4-one, octan-2-one, octan-3-one, nonan-2-one, nonan-3-one, decan-2-one, undecan-2-one, undecan-6-one, pent-3-en-2-one, hex-4-en-3-one, 2-methyl-3-heptanone, 5-methyl-2-hepten-4-one, 2,6-dimethyl-4-heptanone, 6-methylhept-5-en-2-one, oct-1-en-3-one, oct-2-en-4-one, oct-3-en-2-one, dec-3-en-2-one, 4-phenyl-3-buten-2-one, ethyl vinyl ketone, cyclohex-2-en-one, alpha-ionone, camphor, carvone, damascenone, beta-damascene, fenchone, geranylacetone, iso-menthone, nootkatone and zingerone.

* * * * *